(12) United States Patent
Luu et al.

(10) Patent No.: US 11,779,674 B2
(45) Date of Patent: Oct. 10, 2023

(54) VEHICLE AIR FILTRATION SYSTEM

(71) Applicant: Ford Global Technologies, LLC, Dearborn, MI (US)

(72) Inventors: Tai Luu, Westland, MI (US); Doug Vi Luu, Westland, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 577 days.

(21) Appl. No.: 17/060,502

(22) Filed: Oct. 1, 2020

(65) Prior Publication Data
US 2022/0105785 A1 Apr. 7, 2022

(51) Int. Cl.
| | |
|---|---|
| *A61L 9/20* | (2006.01) |
| *B60H 3/06* | (2006.01) |
| *B60R 13/02* | (2006.01) |
| *B60N 2/01* | (2006.01) |
| *B60Q 3/68* | (2017.01) |
| *B60Q 3/30* | (2017.01) |
| *B01D 46/00* | (2022.01) |
| *B01D 46/46* | (2006.01) |

(52) U.S. Cl.
CPC ............ *A61L 9/20* (2013.01); *B01D 46/0028* (2013.01); *B01D 46/46* (2013.01); *B60H 3/0658* (2013.01); *B60N 2/01* (2013.01); *B60Q 3/30* (2017.02); *B60Q 3/68* (2017.02); *B60R 13/0212* (2013.01); *A61L 2209/111* (2013.01); *A61L 2209/14* (2013.01); *A61L 2209/16* (2013.01); *B01D 2279/40* (2013.01)

(58) Field of Classification Search
CPC ........... A61L 9/18–205; A61L 2209/11; A61L 2209/14; B01D 46/0028; B01D 46/44–46; B01D 2279/40; B60H 3/06–0658; B60N 2/01; B60Q 3/30; B60Q 3/68; B60R 13/0212–0231
See application file for complete search history.

(56) References Cited

U.S. PATENT DOCUMENTS

| 6,773,477 | B2 | 8/2004 | Lindsay |
| 6,868,900 | B2 | 3/2005 | Dage et al. |
| 10,266,031 | B2 | 4/2019 | Steinman et al. |
| 10,279,650 | B2 | 5/2019 | Maranville et al. |
| 10,682,895 | B2 * | 6/2020 | Mathiasson .......... B60H 3/0658 |

(Continued)

FOREIGN PATENT DOCUMENTS

| CN | 104108295 B | 6/2017 |
| JP | 6283014 B2 | 2/2018 |

*Primary Examiner* — Jason M Han
(74) *Attorney, Agent, or Firm* — Vichit Chea; Price Heneveld LLP

(57) ABSTRACT

An air filtration system for a vehicle includes a first inlet assembly. A second inlet assembly is in fluid communication with the first inlet assembly. A first fan is disposed within a housing and is in fluid communication with the first inlet assembly. A second fan is disposed within the housing and is in fluid communication with the second inlet assembly. A light source is disposed within the housing proximate the first and second fans. The light source emits ultraviolet light. A filter is disposed within the housing proximate the first and second fans. An outlet is in fluid communication with the first and second inlet assemblies. Air is drawn into the housing by the first and second fans, subjected to the ultraviolet light, and expelled via the outlet.

20 Claims, 9 Drawing Sheets

(56) References Cited

U.S. PATENT DOCUMENTS

| | | |
|---|---|---|
| 2013/0232996 A1 | 9/2013 | Goenka et al. |
| 2020/0062076 A1 | 2/2020 | Elson et al. |
| 2020/0164723 A1 | 5/2020 | Ferri et al. |

* cited by examiner

VEHICLE AIR FILTRATION SYSTEM

FIELD OF THE DISCLOSURE

The present disclosure generally relates to an air filtration system. More specifically, the present disclosure relates to an air filtration system for a vehicle.

BACKGROUND OF THE DISCLOSURE

The air within vehicles may be recirculated. The air may be drawn from within an interior of the vehicle, processed, and returned to the interior. Additionally, outside air may be inserted into the interior of the vehicle.

SUMMARY OF THE DISCLOSURE

According to at least one aspect of the present disclosure, a vehicle air filtration system includes a headliner. At least one inlet assembly is coupled to the headliner and is in fluid communication with an interior compartment. An air filter assembly is coupled to the headliner and is in fluid communication with the interior compartment. The air filter assembly includes at least one fan in fluid communication with the at least one inlet assembly via a duct. A first air filter is disposed proximate the at least one fan. A light source is disposed proximate the first air filter. The light source emits ultraviolet light. A heating, ventilation, and air conditioning system is in fluid communication with the air filter assembly. The heating, ventilation, and air condition system includes a second air filter. A vent assembly is in fluid communication with the interior compartment and the heating, ventilation, and air conditioning system. An airflow path extends from the at least one inlet assembly, through the air filter assembly, through the heating, ventilation, and air conditioning system, and through the vent assembly into the interior compartment.

According to another aspect of the present disclosure, an air filtration system for a vehicle includes a first inlet assembly. A second inlet assembly is in fluid communication with the first inlet assembly. A first fan is disposed within a housing and is in fluid communication with the first inlet assembly. A second fan is disposed within the housing and is in fluid communication with the second inlet assembly. A light source is disposed within the housing proximate the first and second fans. The light source emits ultraviolet light. A filter is disposed within the housing proximate the first and second fans. An outlet is in fluid communication with the first and second inlet assemblies. Air is drawn into the housing by the first and second fans, subjected to the ultraviolet light, and expelled via the outlet.

According to another aspect of the present disclosure, a method of filtering air in a vehicle includes detecting an activation signal; activating at least one fan in response to the activation signal; drawing air through a headliner inlet assembly into a housing via a vacuum effect produced by the at least one fan; emitting an ultraviolet light within the housing; directing the air through an air filter; and expelling the air into an interior compartment.

These and other aspects, objects, and features of the present disclosure will be understood and appreciated by those skilled in the art upon studying the following specification, claims, and appended drawings.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION

Additional features and advantages of the presently disclosed device will be set forth in the detailed description which follows and will be apparent to those skilled in the art from the description, or recognized by practicing the device as described in the following description, together with the claims and appended drawings.

Figure 1:
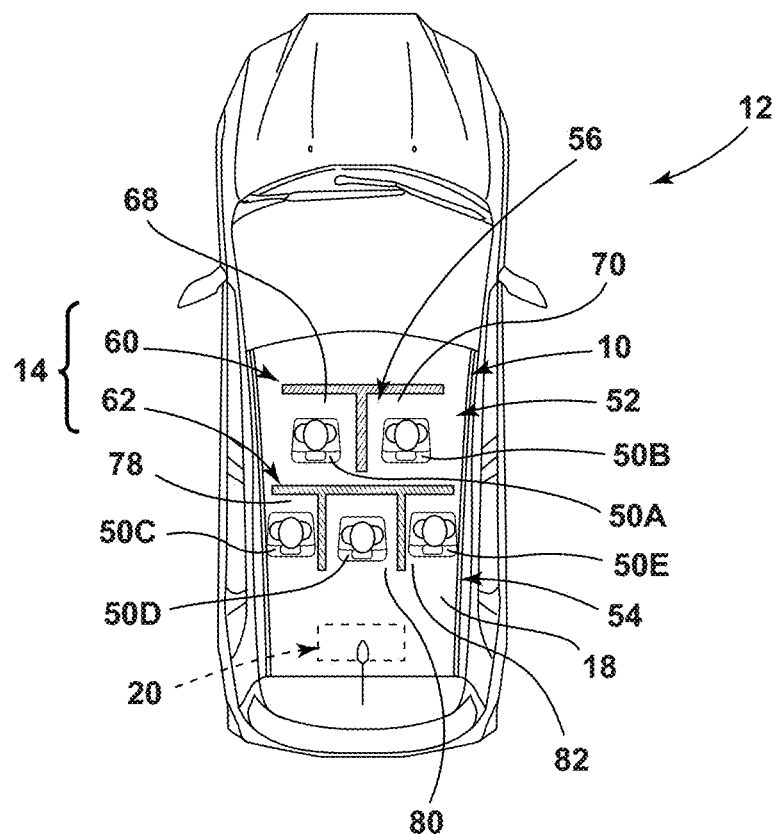
FIG. 1 is a top schematic view of an interior compartment of a vehicle with zones, according to the present disclosure.

For purposes of description herein, the terms "upper," "lower," "right," "left," "rear," "front," "vertical," "horizontal," and derivatives thereof shall relate to the concepts as oriented in FIG. 1. However, it is to be understood that the concepts may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point, and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

As used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Referring to FIGS. 1-10, reference numeral 10 generally designates an air filtration system for a vehicle 12. At least one inlet assembly 14 is coupled to a headliner 16 and is in fluid communication with an interior compartment 18 of the vehicle 12. An air filter assembly 20 is coupled to the headliner 16 and is in fluid communication with the interior compartment 18. The air filter assembly 20 includes at least one fan 22 in fluid communication with the inlet assembly 14 via a duct 24, a first air filter 26 disposed proximate the fan 22, and a light source 28 disposed proximate the first air filter 26. The light source 28 emits ultraviolet (UV) light. A heating, ventilation, and air conditioning (HVAC) system 30 is in fluid communication with the air filter assembly 20. The HVAC system 30 includes a second air filter 32. A vent assembly 34 is in fluid communication with the interior compartment 18 and the HVAC system 30. An airflow path 36 extends from the inlet assembly 14, through the air filter assembly 20, through the HVAC system 30, and through the vent assembly 34 to be expelled into the interior compartment 18.

Figure 2:
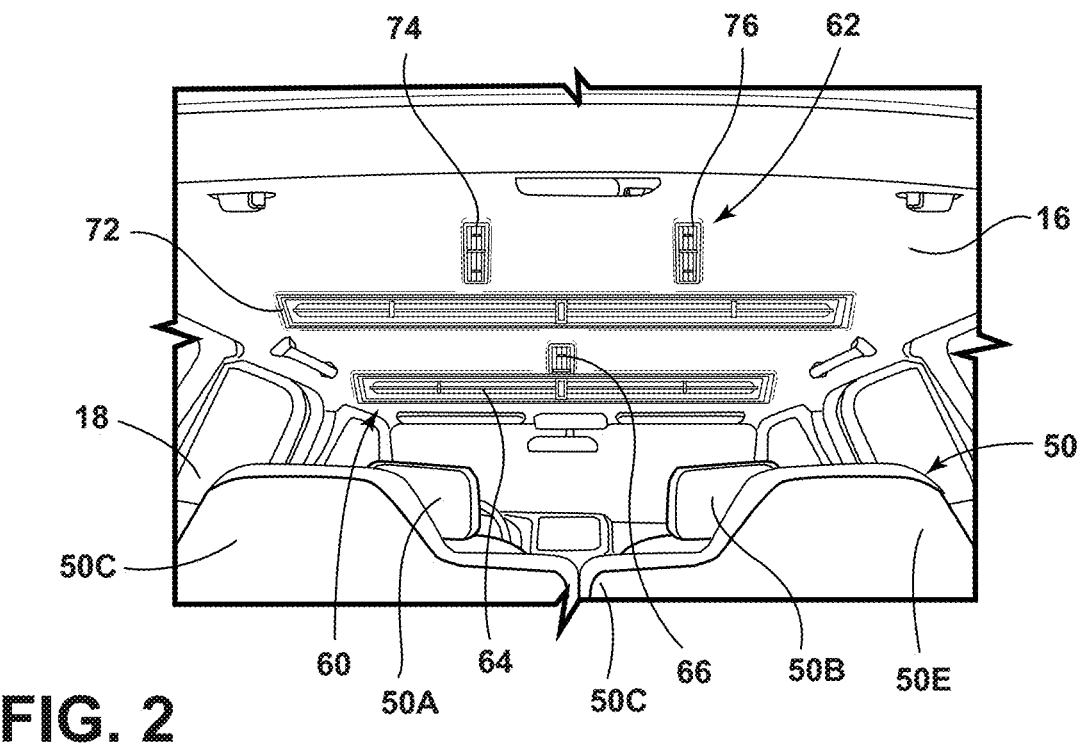
FIG. 2 is a partial rear perspective view of a headliner of a vehicle, according to the present disclosure.

Referring to FIGS. 1 and 2, the vehicle 12 includes multiple seating assemblies 50 arranged within the interior compartment 18. As illustrated in FIGS. 1 and 2, the first seating row 52 includes two seating assemblies 50, and the second seating row 54 includes three seating assemblies 50. Accordingly, seating assemblies 50A, 50B are generally arranged in a first seating row 52, and seating assemblies 50C-50E are generally arranged in a second seating row 54. The seating assemblies 50A-50E are collectively referred to herein as the seating assemblies 50. The first seating row 52 is disposed in a vehicle-forward portion of the interior compartment 18 and the second seating row 54 is disposed rearwardly of the first seating row 52. The vehicle 12 may include additional seating assemblies 50 within the first or second seating rows 52, 54 or additional seating rows without departing from the teachings herein.

The vehicle 12 may be a sedan, a sport utility vehicle, a van, a truck, a crossover, or other styles of wheeled motor vehicles 12, or other types of vehicle 12. The vehicle 12 may be a manually operated vehicle 12 (e.g., with a human driver), a fully autonomous vehicle 12 (e.g., with no human driver), or partially autonomous vehicle 12 (e.g., operated with or without a human driver). Additionally, the vehicle 12 may be utilized for personal or commercial purposes, such as, for ride providing services (e.g., chauffeuring) or ride-sharing services.

Referring still to FIGS. 1 and 2, the vehicle 12 includes the air filtration system 10 for sanitizing and filtering the air within the interior compartment 18. The air filtration system 10 divides the interior compartment 18 into zones 56. Each zone 56 includes one seating assembly 50, which assists in sanitizing and filtering the air around each seating assembly 50, and accordingly, each passenger on the seating assemblies 50.

The air filtration system 10 includes a first inlet assembly 60 and a second inlet assembly 62, each coupled to the headliner 16 of the vehicle 12 and in fluid communication with the interior compartment 18. Generally, the headliner 16 is adhered or otherwise coupled to an inside of a roof of the vehicle 12. The first inlet assembly 60 is coupled to the headliner 16 proximate the first seating row 52 and the second inlet assembly 62 is coupled to the headliner 16 proximate the second seating row 54.

The first inlet assembly 60 includes a first inlet 64 and a second inlet 66. The first inlet 64 extends in a first, generally cross-car direction proximate each of the seating assemblies 50A, 50B in the first seating row 52. The first inlet 64 is disposed proximate a front edge of each seating assembly 50A, 50B to be positioned in a slightly vehicle-forward location relative to passengers disposed on the seating assemblies 50A, 50B. The second inlet 66 extends in a second, generally fore-aft direction. As such, the second inlet 66 extends generally perpendicular to the first inlet 64. The second inlet 66 extends in the fore-aft direction between the seating assemblies 50A, 50B of the first seating row 52. The second inlet 66 may be in fluid communication with the first inlet 64. The first and second inlets 64, 66 of the first inlet assembly 60 divides the interior compartment 18 into a first zone 68 and a second zone 70.

The second inlet assembly 62 includes a first inlet 72, a second inlet 74, and third inlet 76, which may be in fluid communication with one another. The first inlet 72 extends in the first, generally cross-car direction proximate each of the seating assemblies 50C, 50D, 50E of the second seating row 54. The first inlet 72 is disposed proximate a front edge of each seating assembly 50C, 50D, 50E to be positioned in a slightly vehicle-forward location relative to passengers disposed on the seating assemblies 50C, 50D, 50E. The second inlet 74 extends in the second, generally fore-aft direction between the seating assemblies 50C, 50D of the second seating row 54. The third inlet 76 extends in the second, generally fore-aft direction between the seating assemblies 50D, 50E. Accordingly, the second inlet assembly 62 further divides the interior compartment 18 into third, fourth, and fifth zone 78, 80, 82. Each of the first zone 68 and the second zone 70 in the first seating row 52 and the third zone 78, the fourth zone 80, and the fifth zone 82 of the second seating row 54 are collectively referred to herein as the zones 56.

Each seating assembly 50 within the first seating row 52 and the second seating row 54 is disposed in an individual zone 56 formed by the first and second inlet assemblies 60, 62. It is contemplated that each of the first and second inlets 64, 66 of the first inlet assembly 60 and the first, second, and third inlets 72, 74, 76 of the second inlet assembly 62 may be a single inlet, or alternatively, may be multiple inlets extending in the selected direction within the interior compartment 18. A length of each inlet may be adjusted depending on the vehicle 12. Additionally or alternatively, a width of each inlet may be about one to two inches. However, it is contemplated that the first and second inlet assemblies 60, 62 may have any practicable configuration without departing from the teachings herein.

Figure 3:
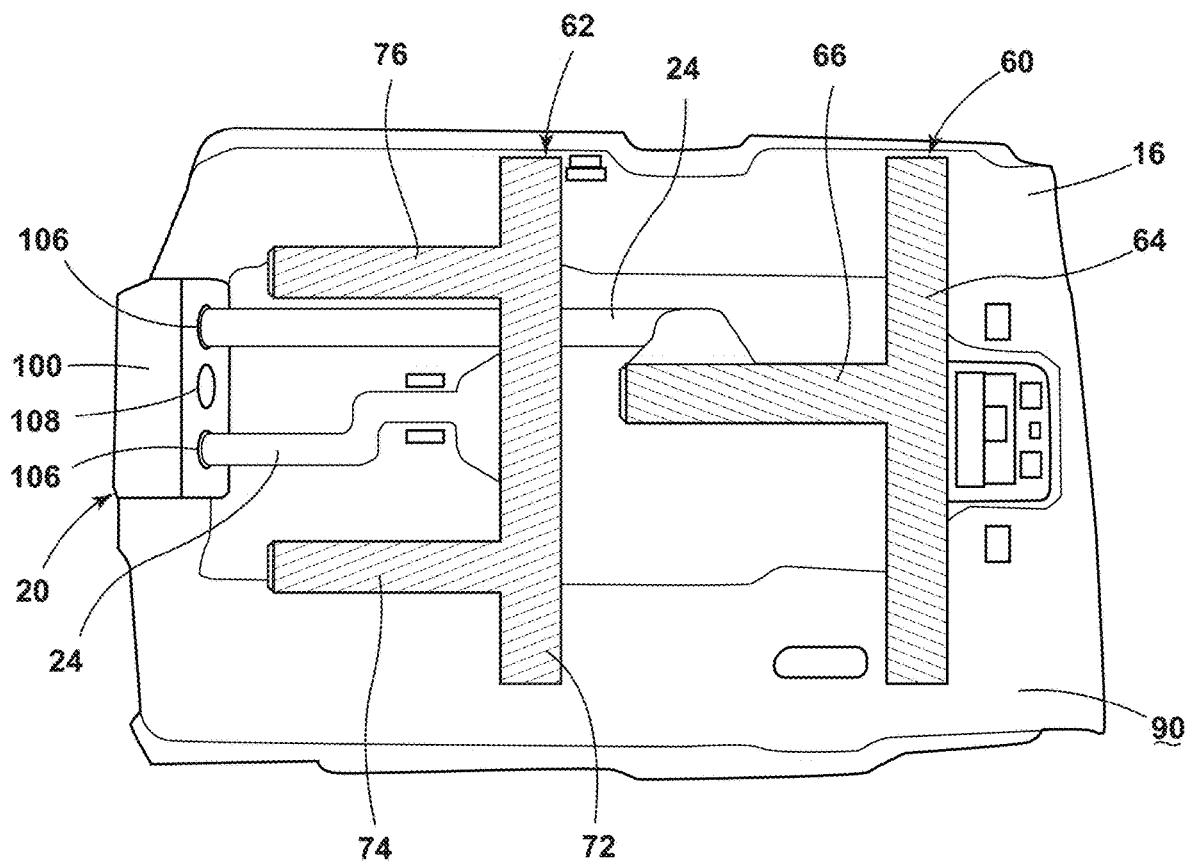
FIG. 3 is a top schematic view of an air filtration system coupled to an inside surface of a vehicle headliner, according to the present disclosure.

Referring still to FIG. 2, as well as FIG. 3, the first inlet assembly 60 and the second inlet assembly 62 are in fluid communication with the interior compartment 18 and with the air filter assembly 20. The air filter assembly 20 is coupled to the headliner 16 in a vehicle-rearward portion of the interior compartment 18. A first duct 24 extends from the first inlet assembly 60 to the air filter assembly 20, and a second duct 24 extends from the second inlet assembly 62 to the air filter assembly 20. The ducts 24 are generally molded into a B-surface 90 of the headliner 16. As used herein, the term "B-surface" refers to a surface of any component within the vehicle 12 that is concealed or non-contactable by the passenger within the vehicle 12 when the component is in an assembled state. It is also contemplated that the ducts 24 may be an additional component adhered to or otherwise coupled to the B-surface 90 of the headliner 16. The air filtration system 10 may be substantially obscured from the view of the passengers within the vehicle 12 by the headliner 16.

Figure 4:
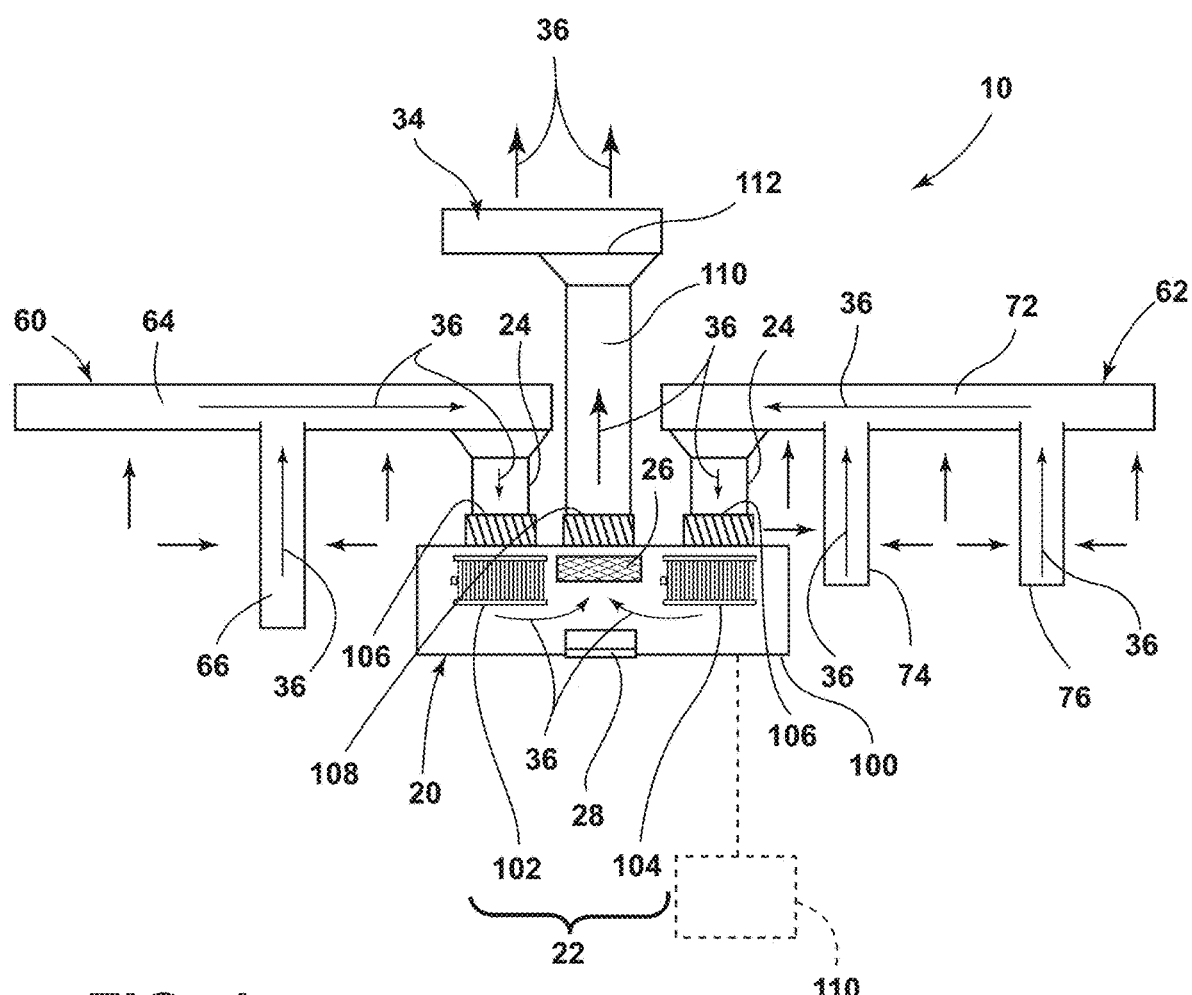
FIG. 4 is a schematic diagram of an air filtration system, according to the present disclosure.
Figure 5:
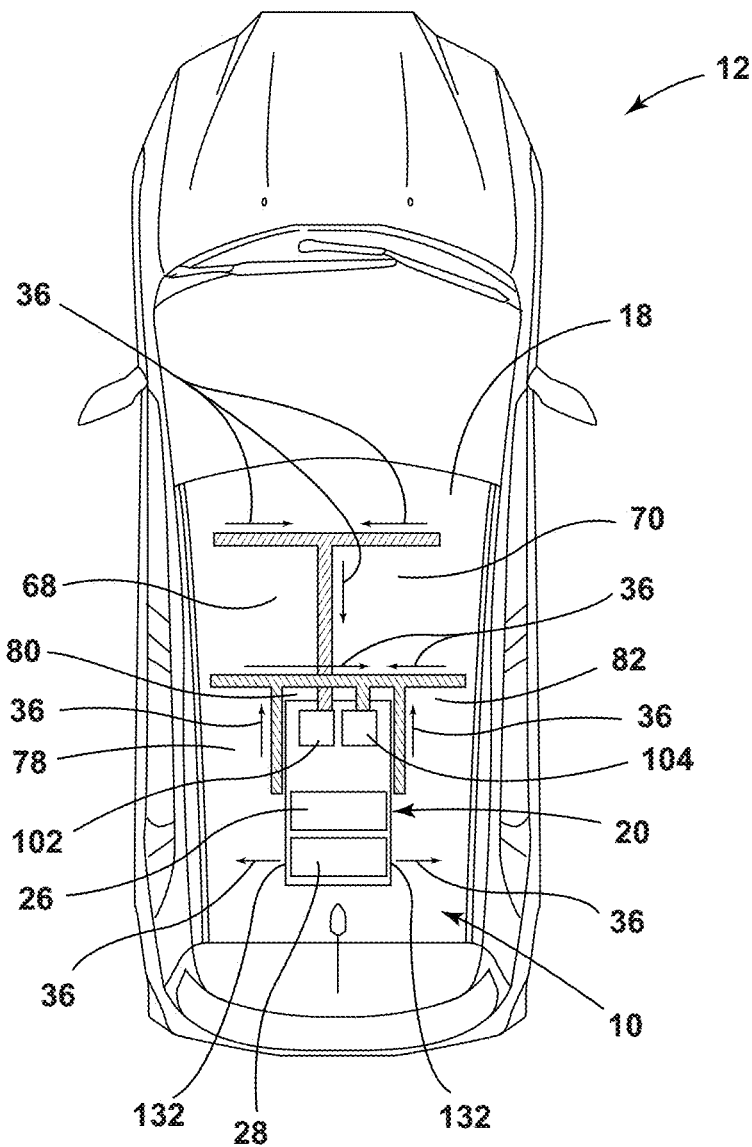
FIG. 5 is a schematic view of an air filtration system within a vehicle, according to the present disclosure.

Referring to FIGS. 4 and 5, the air filtration system 10 may be a stand-alone system coupled with the headliner 16 that operates to filter and sanitize air within the interior compartment 18. As previously stated, each of the first and second inlet assemblies 60, 62 is in fluid communication with the air filter assembly 20. The air filter assembly 20 includes a housing 100, with first and second fans 102, 104, the first air filter 26, and the light source 28 disposed within the housing 100. The housing 100 includes two inlet ports 106, each coupled to a respective duct 24 in fluid communication with the first and second inlet assemblies 60, 62, and an outlet port 108 coupled to a duct 110 in fluid communication with an outlet 112. As illustrated, the outlet port 108 is centrally located between the inlet ports 106, however, any practicable configuration is contemplated without departing from the teachings herein.

The first and second fans 102, 104 are disposed proximate the respective inlet port 106 of the housing 100 to draw air from the interior compartment 18. The first fan 102 is associated with the first inlet assembly 60, and the second fan 104 is associated with the second inlet assembly 62. Each of the first and second fans 102, 104 may be operably coupled with a fan motor. It is also contemplated that the first and second fans 102, 104 may be configured as a blower motor. In such examples, the first and second fans 102, 104 may be single speed blower motors, or alternatively, variable speed blower motors. The first and second fans 102, 104 may have any practicable configuration for directing air in the selected airflow path 36 without departing from the teachings herein.

The first fan 102 draws air through the first inlet assembly 60 through a suction or vacuum effect and directs the air into the housing 100 via the duct 24. The first inlet assembly 60 includes the first inlet 64 proximate each of the seating assemblies 50A, 50B of the first seating row 52, and the second inlet 66 disposed between the seating assemblies 50A, 50B. The second inlet 66 may be oriented to allow air to be drawn from both of the first and second zones 68, 70 through the second inlet 66. The first fan 102 operates to draw air from a vehicle-front and at least one side of each of the first and second zones 68, 70 based on the configuration of the first inlet assembly 60.

The second fan 104 is associated with the second inlet assembly 62. The second fan 104 operates to draw air through the first, second, and third inlets 72, 74, 76 and into the housing 100 via the duct 24. The second inlet 74 extending between the seating assemblies 50C, 50D may be oriented to allow air to be drawn from each of the third and fourth zones 78, 80 through the second inlet 74. Similarly, the third inlet 76 extending between the seating assemblies 50D, 50E may be oriented to allow air to be drawn from each of the third and fourth zones 78, 80 through the third inlet 76. The second fan 104 operates to draw air from a vehicle-front and at least one side of each of the third, fourth, and fifth zones 78, 80, 82 based on the configuration of the second inlet assembly 62. Accordingly, each zone 56 is free from substantial fluid communication with the adjacent zones 56 by at least one of the inlets of one or both of the first and second inlet assemblies 60, 62.

Referring still to FIGS. 4 and 5, a controller 120 is communicatively coupled with each of the first and second fans 102, 104. The controller 120 activates one or both of the first and second fans 102, 104 to draw air from the interior compartment 18, through the first and second inlet assemblies 60, 62, through the ducts 24, and into the housing 100. Additionally or alternatively, the controller 120 is communicatively coupled with the light source 28 of the air filter assembly 20. When at least one of the first and second fans 102, 104 is activated, the controller 120 may also activate the light source 28 to emit the UV light into the housing 100. The light source 28 is generally disposed between the first and second fans 102, 104, such that the airflow path 36 created by each of the first and second fans 102, 104 extends past the light source 28. The light source 28 may be positioned or configured to emit the UV light in a substantial portion, or all, of an interior of the housing 100. Accordingly, the air being drawn into the housing 100 is subjected to the UV light, which may be advantageous for sanitizing the air.

Generally, the UV light emitted by the light source 28 is UV-C light, which may be used to disinfect or sanitize the air drawn in from the interior compartment 18. The UV-C light may have a wavelength in a range of from about 100 nm to about 280 nm. The UV-C light may be advantageous for killing or preventing growth of contamination within the air. Contamination may include dust, pollen, mold, bacteria, viruses, other infectious particles, or other airborne particles. The light source 28 is disposed within housing 100 proximate the first and second fans 102, 104 such that air moved through housing 100 by the first and second fans 102, 104 is subjected to the UV light emitted by the light source 28. It is contemplated that the light source 28 may emit light within the entire UV spectrum, and therefore, may have a wavelength in a range from about 100 nm to about 400 nm without departing from the teachings herein.

The light source 28 may include any form of lighting. For example, fluorescent lighting, light-emitting diodes (LEDs), organic LEDs (OLEDs), polymer LEDs (PLEDs), laser diodes, quantum dot LEDs (QD-LEDs), solid-state lighting, a hybrid, or any other similar device. Any other form of lighting may be utilized within the air filtration system 10 without departing the teachings herein. Further, various types of LEDs are suitable for use as the light source 28, including, but not limited to, top-emitting LEDs, side-emitting LEDs, and others. Moreover, according to various examples, multicolored light sources such as Red, Green, and Blue (RGB) LEDs that may employ red, green, blue LED packaging may be used to generate various desired colors of light outputs from a single light source, according to known light color mixing techniques.

The light source 28 may be configured as a single light. In a non-limiting example, the light source 28 may be a single LED. Alternatively, the light source 28 may be configured as multiple lights and may be disposed in various locations within the housing 100. In examples where the light source 28 is configured as multiple lights, the controller 120 may selectively control each light of the light source 28, such that one, all, or portion of the lights can be activated at any given time. The air filtration system 10 may include one or more circuits or circuit boards coupled to the light source 28, which may be printed circuit boards, such as flexible or rigid printed circuit boards.

Referring to FIGS. 4 and 5, after being subjected to the UV light, the air travels through the first air filter 26 prior to being expelled from the air filter assembly 20. The first air filter 26 is disposed between the first and second fans 102, 104 proximate the outlet port 108, thereby forcing the air through the first air filter 26 before being expelled from the air filter assembly 20. The first air filter 26 may be a high efficiency particulate air (HEPA) filter. The HEPA air filter 26 may filter additional contamination out of the air passing through the housing 100. HEPA filters are generally pleated mechanical air filters that capture contamination with particles having a size in a range from 0.3 µm to about 10 µm.

HEPA filters may be interlaced glass fibers that are arranged to create a fibrous web. As the contamination particles traverse the fibrous web, the fibrous web removes the particles from circulation through a variety of methods, including, but not limited to, direct impaction, sieving, interception, diffusion, or combination thereof. With direct impaction, large contaminants interact with and stick to the fiber. With sieving, the air carries particles between two fibers of the HEPA filter. If the particle is larger than the gap between the two adjacent fibers, the particle becomes trapped by the fibers. With interception, the air moving through the fibers reroutes to travel through gaps between adjacent fibers. The particles in the air may not reroute due to inertia and, therefore, may stick to sides of the fibers. With diffusion, smaller particles may move more erratically than larger particles and are therefore more likely to interact with and stick to the fibers of the HEPA filter. The first air filter 26 is configured to trap particles in the air. As such, the air filter assembly 20 operates to sanitize and filter the air traveling along the airflow path 36.

After traveling through the first air filter 26, the air travels through the duct 110 and is expelled through the outlet 112. In the illustrated configuration of FIGS. 4 and 5, the outlet 112 is coupled to or defined by the headliner 16. The outlet 112 may be in fluid communication with the vent assembly 34, which may be coupled to the headliner 16 to direct the air into the interior compartment 18. The air filtration system 10 may include two vents 132 to direct air in opposing cross-car directions. Alternatively, the vents 132 may direct air in the fore-aft direction within the vehicle 12. The vents 132 are generally disposed in a vehicle-rearward portion of the interior compartment 18.

Referring still to FIGS. 4 and 5, in operation, the controller 120 activates one or both of the first and second fans 102, 104 to produce or create the vacuum effect that draws air from the interior compartment 18 and through the first and second inlet assemblies 60, 62. The air being drawn into the first and second inlet assemblies 60, 62 may include contaminants exhaled or otherwise deposited in the interior compartment 18 by the passengers within the vehicle 12. The configuration of the first and second inlet assemblies 60, 62 defining the various zones 56 within the interior compartment 18 reduces cross-contamination between the zones 56. The first inlets 64, 72 are arranged to be positioned in front of the passenger disposed on the respective seating assembly 50. The second inlets 66, 74 and the third inlet 76 are arranged to a side of each passenger and between passengers seated on adjacent seating assemblies 50. When the air filtration system 10 is activated, the air is drawn from a front and at least one side of each passenger within the vehicle 12 reducing contamination within the air and contamination spread between different zones 56.

The air is drawn through the first and second inlet assemblies 60, 62, through the ducts 24, and into the housing 100. While in the housing 100, the air is subjected to the UV light emitted by the light source 28, which sanitizes the air. The air is then directed through the first air filter 26 to filter the sanitized air. The air is then directed through the duct 110, through the outlet 112, and through the vents 132 to be expelled into the interior compartment 18. Accordingly, the airflow path 36 extends from the interior compartment 18, through the first and second inlet assemblies 60, 62, through the housing 100, through the outlet 112, and returns to the interior compartment 18. The air filtration system 10 operates to collect air that may have contaminants, sanitize and filter the air, and return the air into the interior compartment 18 with a reduced number of contaminants.

Figure 6:
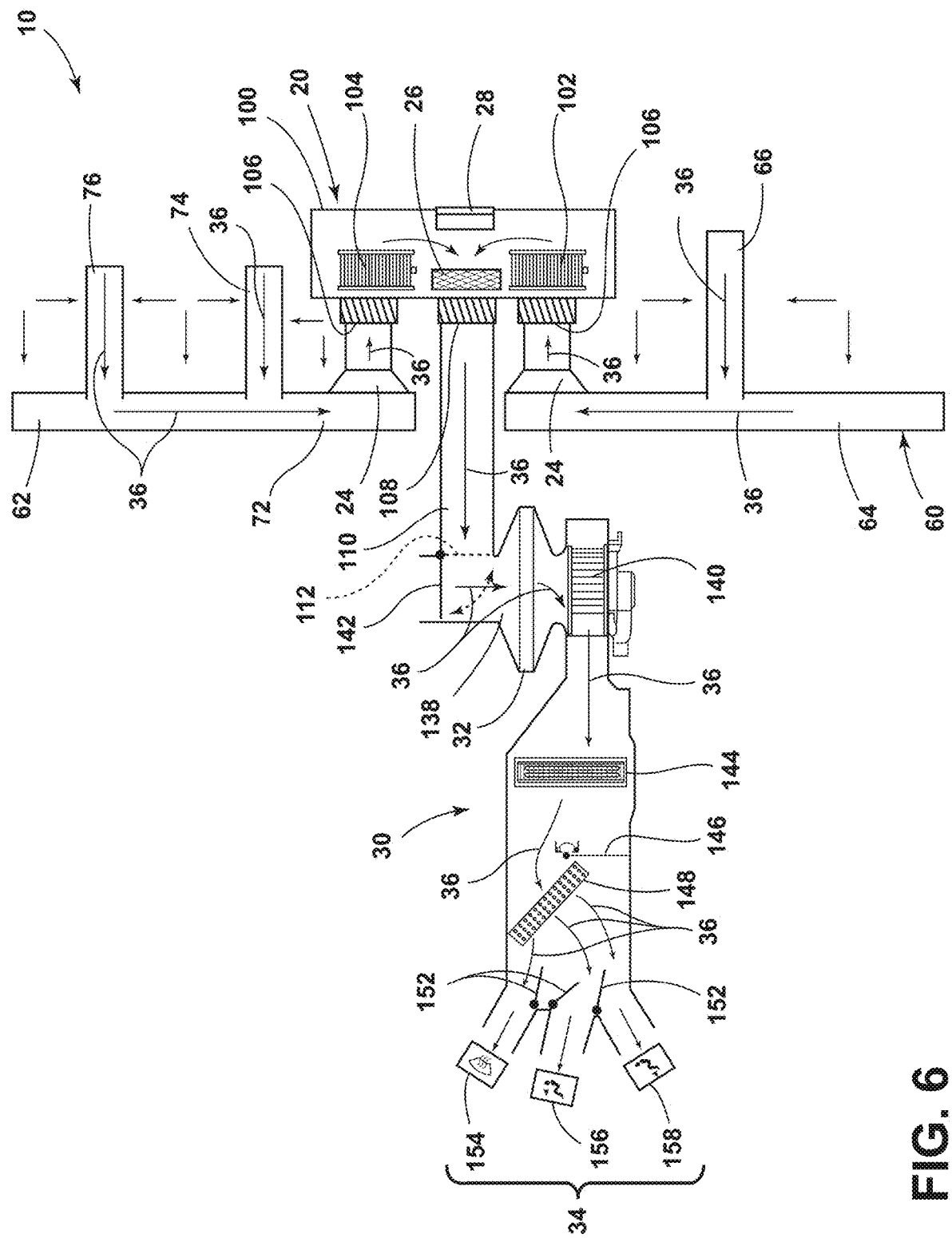
FIG. 6 is a schematic diagram of an air filtration system integrated with a heating, ventilation, and air conditioning system, according to the present disclosure.

Referring to FIG. 6, in an additional or alternative configuration, the air filtration system 10 may be integrated with the HVAC system 30 of the vehicle 12. The air filtration system 10 operates to draw air through the first and second inlet assemblies 60, 62 via the first and second fans 102, 104, as previously described. The air is subjected to the UV light emitted by the light source 28 and passes through the first air filter 26. The air is then directed through the duct 110 and the outlet 112. The duct 110 may extend to engage the HVAC system 30, which is generally positioned in a vehicle-forward portion of the vehicle 12. The outlet 112 is in fluid communication with the HVAC system 30, such that the air being expelled by the air filter assembly 20 is directed into and through the HVAC system 30. The HVAC system 30 generally cleans, cools, heats, regulates, ventilates, and/or dehumidifies the air directed into the interior compartment 18.

The air exiting the air filter assembly 20 is drawn into the duct 110 of the HVAC system 30 by an HVAC fan 140 when a fresh/recirculation door 142 is in a recirculation position. When the fresh/recirculation door 142 is in an outside air position, the air being expelled from the air filter assembly 20 may be blocked or redirected, allowing outside air to be drawn into the HVAC system 30. When in the fresh/recirculation door 142 is in the recirculation position, the air from the air filter assembly 20 travels through the second air filter 32, proximate the HVAC fan 140, and through an evaporator 144. Based on a position of a temperature blended door 146, the air may be directed from the evaporator 144 to a heat exchanger 148, or alternatively, may be directed to bypass the heat exchanger 148. The air is then directed to the vent assembly 34.

Referring still to FIG. 6, vent doors 152 may assist in directing the air to the vent assembly 34. In the illustrated example of FIG. 6, the vent assembly 34 includes three vents, including a defrost vent 154, a passenger upper vent 156, and a passenger lower vent 158. The vent doors 152 may open or close the various vents of the vent assembly 34 based on a condition of the HVAC system 30, a user input, etc. The air is directed through the vent assembly 34 and into the interior compartment 18. The vent assembly 34 is generally disposed in a vehicle-forward portion of the vehicle 12 proximate the first seating row 52 (e.g., on a dashboard). However, it is contemplated that the various vents of the vent assembly 34 may be disposed in multiple locations (e.g., dashboards, center consoles, trim panels, etc.) throughout the vehicle 12 without departing from the teachings herein. In this configuration, the airflow path 36 extends from the interior compartment, through the first and second inlet assemblies 60, 62, through the air filter assembly 20, through the HVAC system 30, and through the vent assembly 34 to be returned to the interior compartment 18. The air with contaminants drawn into the air filter assembly 20 may be sanitized and filtered to reduce the number of contaminants, filtered again by the HVAC system 30, and heated or cooled by the HVAC system 30.

Figure 7:
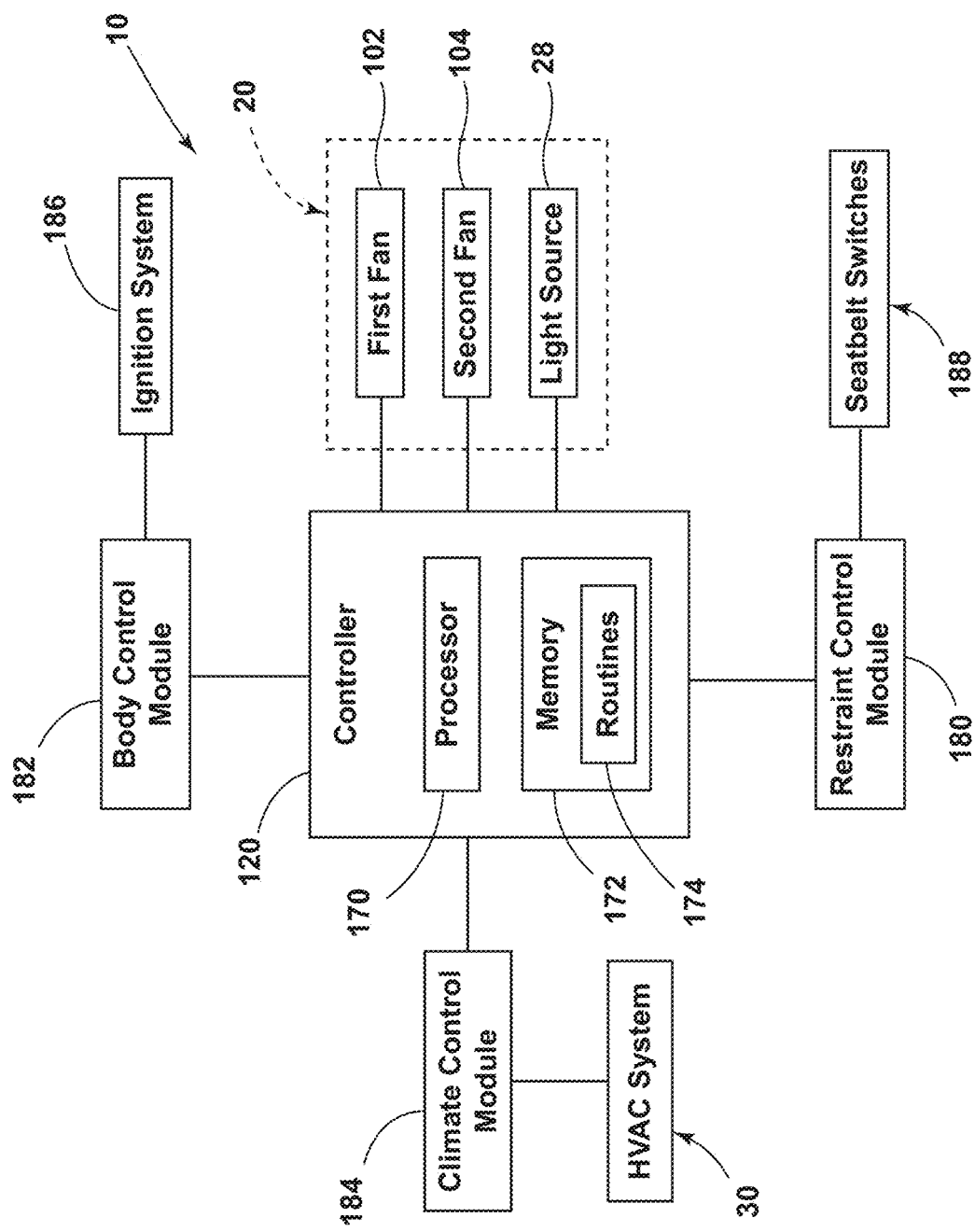
FIG. 7 is a block diagram of an air filtration system, according to the present disclosure.
Figure 8:
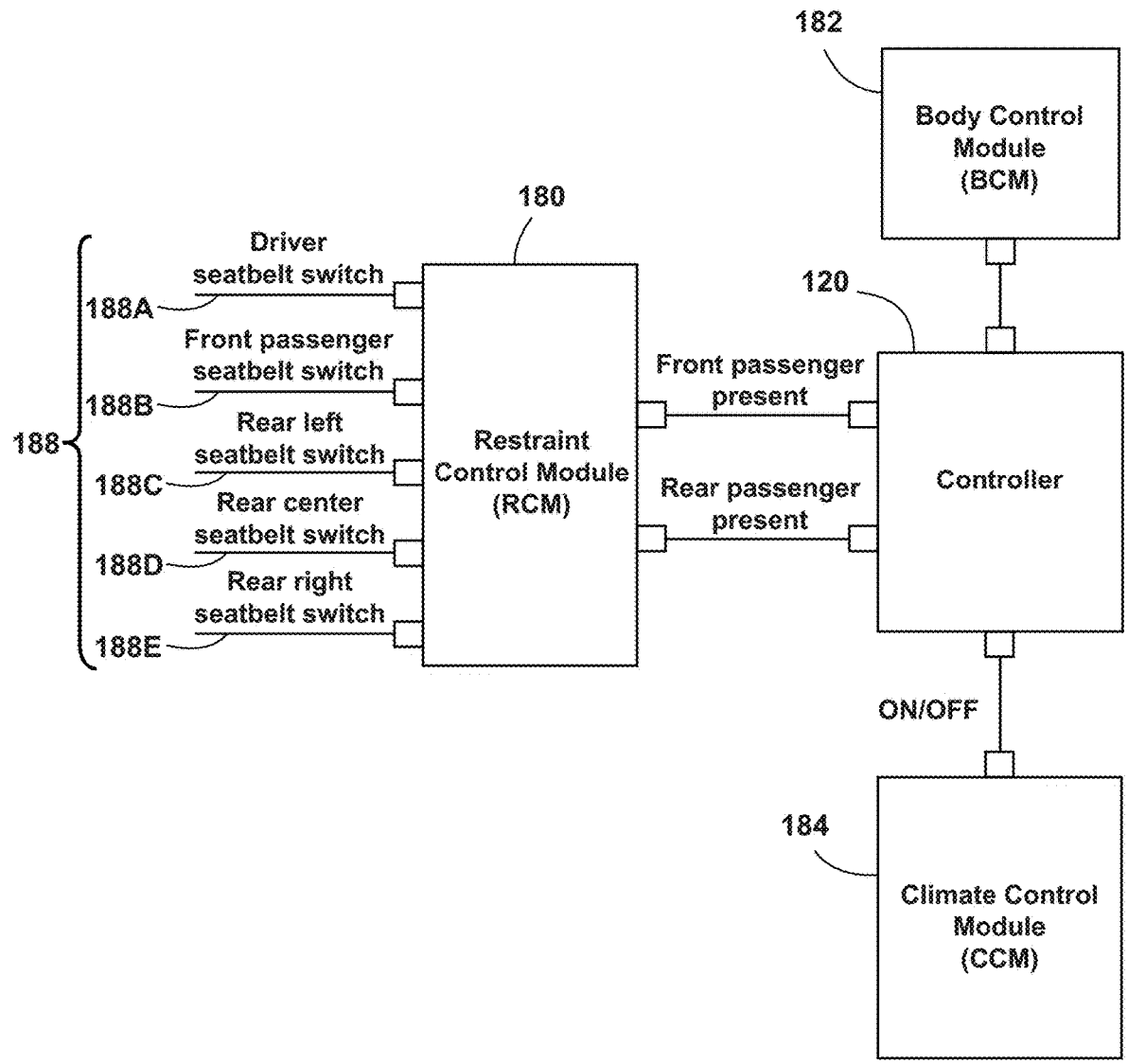
FIG. 8 is a block diagram of an air filtration system in communication with a body control module, a restraint control module, and a climate control module, according to the present disclosure.

Referring to FIGS. 7 and 8, the controller 120 includes a processor 170, a memory 172, and other control circuitry. Instructions or routines 174 are stored within the memory 172 and executable by the processor 170. The controller 120 is communicatively coupled with each of the first and second fans 102, 104 and the light source 28 of the air filter assembly 20. The controller 120 activates the first fan 102, the second fan 104, the light source 28, or a combination thereof in response to an activation signal. The activation signal may be communicated to the controller 120 from at least one of a restraint control module 180, a body control module 182, and a climate control module 184 of the vehicle 12.

The activation signal may be a signal from the body control module 182 in response to a status from an ignition system 186. For example, when the ignition system 186 is activated (e.g., the ignition is "on"), the air filter assembly 20 may be activated. The body control module 182 detects that the vehicle ignition is activated and communicates the status with the controller 120, and the controller 120 then at least partially activates the air filter assembly 20. Additionally or alternatively, after receiving the signal from the body control module 182, the controller 120 may communicate with the restraint control module 180 to determine which aspects of the air filter assembly 20 to activate.

The activation signal may also be communicated from the restraint control module 180. The restraint control module 180 is communicatively coupled with the controller 120 and detects where passengers are located in the vehicle 12 via seatbelt switches 188. The seatbelt switches 188 include a driver seatbelt switch 188A associated with the seating assembly 50A and a front passenger seatbelt switch 188B associated with the seating assembly 50B. The seatbelt switches 188 also include a rear side seatbelt switch 188C associated with the seating assembly 50C, a rear center seatbelt switch 188D associated with the seating assembly 50D, and a rear side seatbelt switch 188E associated with the seating assembly 50E. As the seatbelt switches 188 correspond with certain seating assemblies 50, the seatbelt switches 188 also correspond to certain zones 56 within the vehicle 12. It is contemplated that additional seating assemblies 50 and seatbelt switches 188 may be included in with vehicle 12 without departing from the teachings herein.

The seatbelt switches 188 detect when seatbelts of the associated seating assembly 50 are engaged or disengaged and communicates the seatbelt status or a seatbelt switch signal to the restraint control module 180. The restraint control module 180 communicates which seatbelt switches 188 are engaged. For example, a first seatbelt switch signal may be communicated from the restraint control module 180 to the controller 120 when a front passenger is present as indicated by the driver seatbelt switch 188A or the front passenger seatbelt switch 188B. A second seatbelt switch signal indicating a rear passenger is present may be communicated to the controller 120 when at least one of the rear seatbelt switches 188C, 188D, 188E indicates a seatbelt engagement. Based on the signal received from the restraint control module 180, the controller 120 may activate one or both of the first and second fans 102, 104 and the light source 28 as described in further detail below.

Referring still to FIGS. 7 and 8, the activation signal may also be communicated to the controller 120 from the climate control module 184. The climate control module 184 is in communication with the HVAC system 30. When the HVAC system 30 is activated, the climate control module 184 communicates a signal to the controller 120 to activate the air filter assembly 20. The air filter assembly 20 in communication with the HVAC system 30 may operate simultaneously with activation and deactivation of the HVAC system 30. It is also contemplated that the standalone air filtration system 10 may activate when the HVAC system 30 is activated or deactivated based on certain passenger settings, inputs, etc. Accordingly, the controller 120 is in communication with the restraint control module 180, the body control module 182, and the climate control module 184 and operates the air filter assembly 20 in response to various signals received from one or more of the restraint control module 180, the body control module 182, and the climate control module 184.

Figure 9:
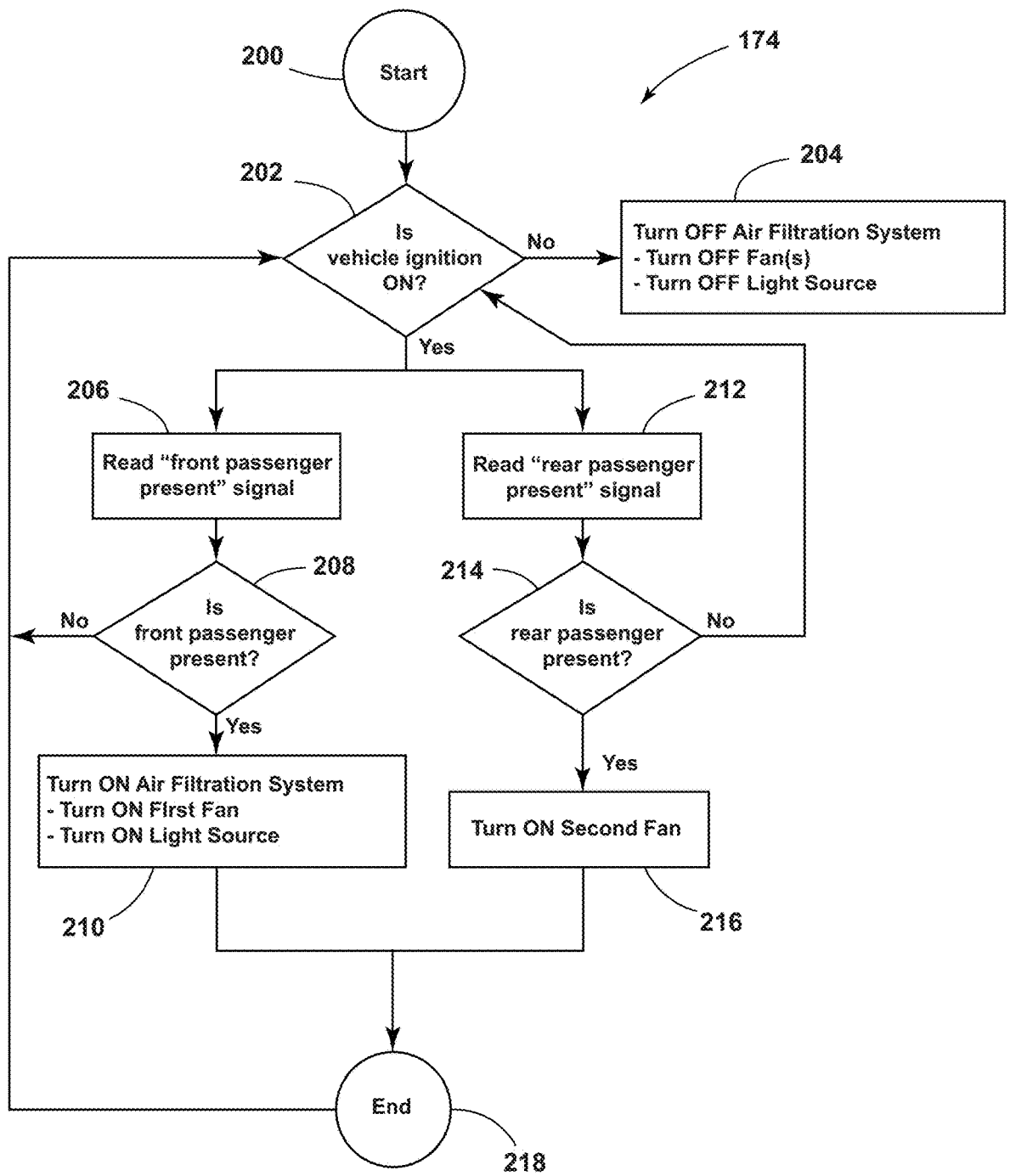
FIG. 9 is a flow diagram of a routine for activating an air filtration system in a vehicle, according to the present disclosure.

Referring to FIG. 9, as well as FIGS. 1-8, an exemplary routine 174 for activating the air filtration system 10 is illustrated. The routine 174 begins at a start 200 and proceeds to decision step 202. In decision step 202, the controller 120 determines whether the vehicle ignition is activated (e.g., "on"). The controller 120 communicates with the body control module 182 at decision step 202 to make this determination. If the vehicle ignition is "off" or deactivated, the routine 174 proceeds to step 204 of maintaining the air filtration system 10 in an "off" or deactivated state. Alternatively, the controller 120 may deactivate the air filtration system 10 from an activated or "on" state. The deactivation of the air filtration system 10 includes deactivating one or both of the first and second fans 102, 104 and deactivating the light source 28. The air filter assembly 20 may remain in the deactivated state until the vehicle ignition is activated.

Returning to decision step 202, if the vehicle ignition is activated, the routine 174 proceeds to step 206 of determining whether a passenger is disposed in the first seating row 52. In step 206, the controller 120 communicates with the restraint control module 180 to determine if a passenger is disposed in the seating assemblies 50A, 50B as indicated by the driver seatbelt switch 188A and the front passenger seatbelt switch 188B.

In decision step 208, the controller 120 determines whether a front passenger is present based on the signal received from the restraint control module 180. A "front passenger present" signal (e.g., the seatbelt switch signal) may be communicated from the restraint control module 180 to the controller 120. The "front passenger present" signal may also indicate which seating assembly 50 the passenger is positioned on. If a front passenger is not present, the routine 174 returns to the decision step 202 to determine whether the vehicle ignition is activated. If, in decision step 208, the controller 120 determines that a front passenger is present within the vehicle 12, the routine 174 proceeds to step 210. In step 210, the air filtration system 10 is at least partially activated. The controller 120 activates the first fan 102 to draw air through the first inlet assembly 60 proximate the first seating row 52. The controller 120 also activates the light source 28 to sanitize the air drawn into the housing 100 through the first inlet assembly 60.

Returning to decision step 202, if the vehicle ignition is "on," the routine 174 additionally or alternatively proceeds to step 212. In step 212, the controller 120 determines whether a passenger is disposed in the second seating row 54. The controller 120 communicates with the restraint control module 180 to determine if a passenger is present in the seating assemblies 50C, 50D, 50E as detected by the rear seatbelt switches 188C, 188D, 188E.

In decision step 214, the controller 120 determines whether a rear passenger is present based on the signal received from the restraint control module 180. A "rear passenger present" signal (e.g., the seatbelt switch signal) may be communicated from the restraint control module 180 to the controller 120. The "rear passenger present" signal may also indicate which seating assembly 50 the passenger is positioned on. If a rear passenger is not present, the routine 174 returns to the decision step 202 to determine whether the vehicle ignition is activated. If, in decision step 214, the controller 120 determines that a rear passenger is present within the vehicle 12, the routine 174 proceeds to step 216.

In step 216, the controller 120 at least partially activates the air filter assembly 20. The first fan 102 and the light source 28 may already be activated based on previously described steps of the routine 174. Accordingly, when a rear passenger is detected, the controller 120 activates the second fan 104 to also draw air through the second inlet assembly 62 proximate the second seating row 54. Accordingly, when a front passenger is detected, the first fan 102 and the light source 28 are activated, and when a rear passenger is detected the first fan 102, the second fan 104, and the light source 28 are activated. The controller 120 may include a manual override option based on a user input that allows the second fan 104 to be activated along with the first fan 102 when a front passenger is detected but no rear passenger is detected.

After activation of the air filter assembly 20, the routine 174 may proceed to an end 218. The routine 174 may return to decision step 202 to monitor the status of the vehicle ignition and passenger locations within the vehicle 12 to control the air filter assembly 20. For example, if a rear passenger exits the vehicle 12, the second fan 104 may be deactivated while the first fan 102 remains active. The routine 174 may be conducted periodically or continuously. Various steps of the routine 174 may be conducted simultaneously or sequentially. For example, the controller 120 may determine whether a front passenger is present in step 206 substantially simultaneously with determining whether a rear passenger is present in step 212. Alternatively, the controller 120 may determine whether a rear passenger in step 212 after activating the air filter system 10 in step 210.

Figure 10:
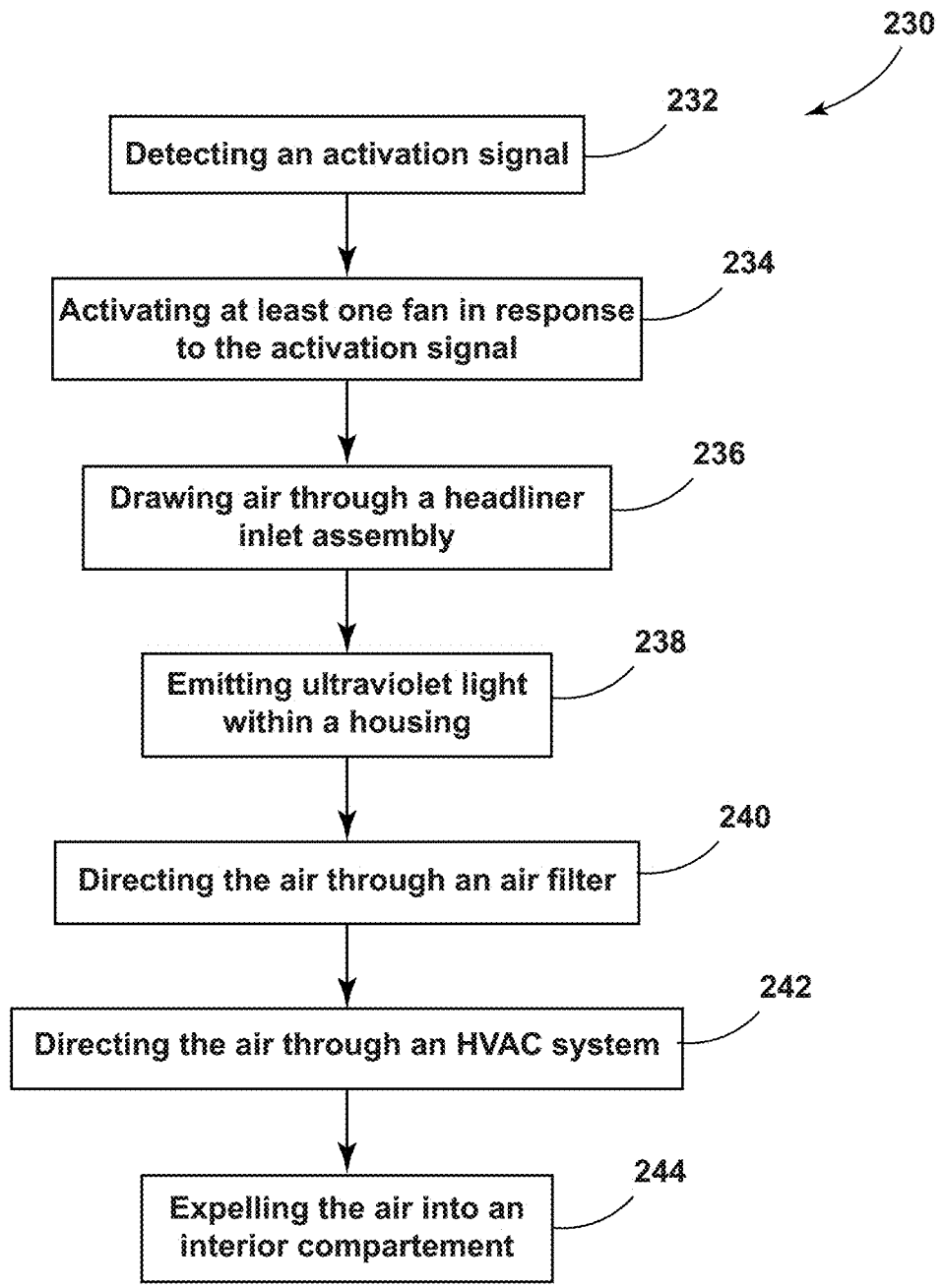
FIG. 10 is a flow diagram of a method for filtering air within a vehicle, according to the present disclosure.

Referring to FIG. 10, as well as FIGS. 1-9, a method 230 of filtering air within the vehicle 12 includes step 232 of detecting the activation signal. The activation signal may include the vehicle ignition activation as detected by the body control module 182, detecting at least one passenger on one of the seating assemblies 50 as detected by the restraint control module 180, activation of the HVAC system 30 as detected by the climate control module 184, or a combination thereof. Upon detecting the activation signal, in step 234, the controller 120 activates at least one of the first and second fans 102, 104 and the light source 28. If the activation signal is communicated from the restraint control module 180, the detected position of the passenger in the vehicle 12 may dictate whether one or both of the first and second fans 102, 104 is activated. If the controller 120 detects passengers in the first seating row 52, the first fan 102 is activated, and if the controller 120 also detects passengers within the second seating row 54, the second fan 104 may be activated along with the first fan 102.

In step 236, with the first and/or second fans 102, 104 activated, the air is drawn through the first and/or second inlet assemblies 60, 62. The air is drawn through the ducts 24 and into the housing 100. In step 238, the UV light is emitted by the light source 28 within the housing 100. Step 238 includes subjecting the air within the housing 100 to the UV light as air travels along the airflow path 36 to sanitize the air before the air travels through the first air filter 26. The UV light, particularly UV-C light, is used to reduce contamination within the air.

In step 240, the air is directed through the first air filter 26, which is generally configured as a HEPA filter. The air is filtered after being sanitized to further reduce contaminants within the air. Step 240 also includes directing the air through the duct 110 and through the outlet 112 to be expelled from the air filter assembly 20.

In step 242, the air is directed through the HVAC system 30. The air is expelled from the outlet 112 and is filtered through the second air filter 32. The air is then guided through the vent assembly 34. During step 242, the air may be heated or cooled by the HVAC system 30. In step 244, the air is expelled into the interior compartment 18. If the air is guided through the vent assembly 34, the air may be expelled in various locations within the interior compartment 18. It is contemplated that at least step 242 may be omitted, and the air may be expelled from the vents 132 coupled to the headliner 16. In such examples, the air may be expelled in a vehicle-rearward portion of the interior compartment 18 after traveling through the air filter assembly 20. It is contemplated that the steps of method 230 may be performed in any order, simultaneously, or omitted without departing from the teachings provided herein.

The air filtration system 10 disclosed herein may be utilized to sanitize and filter the air within the interior compartment 18. In health situations, it may be advantageous for people to remain a certain distance from one another (e.g., about six feet). However, maintaining such distance may be difficult for passengers within vehicles 12. The air filtration system 10 described herein divides the interior compartment 18 into the zones 56 and operates to reduce or minimize fluid communication between the zones 56 and, accordingly, the passengers. The configuration of the first and second inlet assemblies 60, 62 may be advantageous for reducing cross-contamination between zones 56 and reducing contamination within the vehicle 12 to assist in managing certain health situations. The air filtration system 10 may reduce the possibility that one passenger may inhale contamination exhaled by another passenger.

Use of the present device may provide for a variety of advantages. For example, the air filtration system 10 may divide the interior compartment 18 into the zones 56. The zones 56 may correspond with each seating assembly 50 within the vehicle 12. Additionally, the first and second inlet assemblies 60, 62 may be positioned to reduce cross-contamination between different zones 56. Further, the air filtration system 10 may reduce contamination within the air through filtration through the first air filter 26 and sanitation using UV light emitted from the light source 28. Also, the configuration of the first inlet assembly 60 and the second inlet assembly 62 provides each zone 56 with a minimum of two inlets, one disposed to a front of the passenger on the seating assembly 50 and one disposed to at least one side of the passenger. Moreover, the air filtration system 10 may automatically detect where passengers are located within the vehicle 12, and activation of components of the air filtration system 10 may be determined based on the detected location. Additionally, the air filtration system 10 may be in communication with the restraint control module 180, the body control module 182, and the climate control module 184 to receive one or more activation signals to activate the air filter assembly 20. Additionally, the air filtration system 10 may be a standalone system, or alternatively, may be integrated with the HVAC system 30 of the vehicle 12. Additional benefits or advantages of using this device may also be realized and/or achieved.

According to various examples, a vehicle air filtration system includes a headliner. At least one inlet assembly is coupled to the headliner and is in fluid communication with an interior compartment. An air filter assembly is coupled to the headliner and is in fluid communication with the interior compartment. The air filter assembly includes at least one fan in fluid communication with the at least one inlet assembly via a duct. A first air filter is disposed proximate the at least one fan. A light source is disposed proximate the first air filter. The light source emits ultraviolet light. A heating, ventilation, and air conditioning system is in fluid communication with the air filter assembly. The heating, ventilation, and air condition system includes a second air filter. A vent assembly is in fluid communication with the interior compartment and the heating, ventilation, and air conditioning system. An airflow path extends from the at least one inlet assembly, through the air filter assembly, through the heating, ventilation, and air conditioning system, and through the vent assembly into the interior compartment. Embodiments of the present disclosure may include one or a combination of the following features:

the at least one inlet assembly includes a first inlet assembly disposed proximate a first seating row and a second inlet assembly proximate a second seating row;

the first seating row includes a first seating assembly disposed adjacent to a second seating assembly, and wherein the first inlet assembly includes a first inlet extending in a first direction proximate each of the first and second seating assemblies and a second inlet extending in a second direction between the first and second seating assemblies;

the second seating row includes first, second, and third seating assemblies, wherein the second inlet assembly includes a first inlet that extends in a first direction proximate each of the first, second, and third seating assemblies, and wherein the second inlet assembly includes a second inlet that extends in a second direction between the first and second seating assemblies and a third inlet that extends in the second direction between the second and third seating assemblies;

the at least one fan includes a first fan fluidly coupled to the first inlet assembly and a second fan fluidly coupled to the second inlet assembly;

the air filter assembly includes a housing coupled to the headliner, wherein the at least one fan, the light source, and the first air filter are disposed within the housing;

a controller communicatively coupled to the at least one fan, wherein the controller is communicatively coupled to at least one of a restraint control module, a body control module, and a climate control module; and the controller activates the at least one fan to draw air from the interior compartment to the air filter assembly in response to a signal from at least one of the restraint control module, the body control module, and the climate control module.

According to another example, an air filtration system for a vehicle includes a first inlet assembly. A second inlet assembly is in fluid communication with the first inlet assembly. A first fan is disposed within a housing and is in fluid communication with the first inlet assembly. A second fan is disposed within the housing and is in fluid communication with the second inlet assembly. A light source is disposed within the housing proximate the first and second fans. The light source emits ultraviolet light. A filter is disposed within the housing proximate the first and second fans. An outlet is in fluid communication with the first and second inlet assemblies. Air is drawn into the housing by the first and second fans, subjected to the ultraviolet light, and expelled via the outlet. Embodiments of an aspect of the present disclosure can include any one or a combination of the following features:

a controller communicatively coupled to the first and second fans, wherein the controller activates the first and second fans in response to a signal from at least one of a restraint control module, a body control module, and a climate control module;

the controller activates the first fan in response to a first seatbelt switch signal detected by the restraint control module and the second fan is activated in response to a second seatbelt switch signal detected by the restraint control module;

the filter is a high efficiency particulate air filter;

the first inlet assembly includes a first inlet extending in a first direction and a second inlet extending in a second direction, wherein the second inlet assembly includes a first inlet extending in the first direction and a second inlet extending in the second direction, wherein the first direction is different than the second direction;

the outlet is defined in a headliner; and the outlet is in fluid communication with a heating, ventilation, and air conditioning system.

According to yet another example, a method of filtering air in a vehicle includes detecting an activation signal; activating at least one fan in response to the activation signal; drawing air through a headliner inlet assembly into a housing via a vacuum effect produced by the at least one fan; emitting an ultraviolet light within the housing; directing the air through an air filter; and expelling the air into an interior compartment. Embodiments of an aspect of the present disclosure can include any one or a combination of the following features:

the step of detecting the activation signal includes detecting at least one of a passenger on a seating assembly, a vehicle ignition activation, and an activation of a heating, ventilation, and air conditioning system as the activation signal;

the step of drawing air through the headliner inlet assembly includes drawing the air from proximate a first seating row in the interior compartment through a first inlet of the headliner inlet assembly via a first fan of the at least one fan and drawing the air from proximate a second seating row in the interior compartment through a second inlet of the headliner inlet assembly via a second fan of the at least one fan;

directing the air through a heating, ventilation, and air conditioning system; and the step of emitting the ultraviolet light within the housing includes subjecting the air to the ultraviolet light as the air travels through the housing before traveling through the air filter.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

The various illustrative logical blocks, modules, controllers, and circuits described in connection with the embodiments disclosed herein may be implemented or performed with application specific integrated circuits (ASICs), field programmable gate arrays (FPGAs), general purpose processors, digital signal processors (DSPs) or other logic devices, discrete gates or transistor logic, discrete hardware components, or any combination thereof designed to perform the functions described herein. A general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

Computer-executable instructions include, for example, instructions and data, which, when executed at a processor, cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

It is also important to note that the construction and arrangement of the elements of the invention as shown in the exemplary examples is illustrative only. Although only a few examples of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary examples without departing from the spirit of the present innovations.

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims, as interpreted according to the principles of patent law, including the doctrine of equivalents.

It is to be understood that variations and modifications can be made on the aforementioned structure without departing from the concepts of the present disclosure, and further it is to be understood that such concepts are intended to be covered by the following claims unless these claims by their language expressly state otherwise.

What is claimed is:

1. A vehicle air filtration system, comprising:
    a headliner;
    at least one inlet assembly coupled to the headliner and in fluid communication with an interior compartment;
    an air filter assembly coupled to the headliner and in fluid communication with the interior compartment, wherein the air filter assembly includes:
        at least one fan in fluid communication with the at least one inlet assembly via a duct;
        a first air filter disposed proximate the at least one fan; and
        a light source disposed proximate the first air filter, wherein the light source emits ultraviolet light;
    a heating, ventilation, and air conditioning system in fluid communication with the air filter assembly, wherein the heating, ventilation, and air condition system includes a second air filter; and
    a vent assembly in fluid communication with the interior compartment and the heating, ventilation, and air conditioning system, wherein an airflow path extends from the at least one inlet assembly, through the air filter assembly, through the heating, ventilation, and air conditioning system, and through the vent assembly into the interior compartment.

2. The vehicle air filtration system of claim 1, wherein the at least one inlet assembly includes a first inlet assembly disposed proximate a first seating row and a second inlet assembly proximate a second seating row.

3. The vehicle air filtration system of claim 2, wherein the first seating row includes a first seating assembly disposed adjacent to a second seating assembly, and wherein the first inlet assembly includes a first inlet extending in a first direction proximate each of the first and second seating assemblies and a second inlet extending in a second direction between the first and second seating assemblies.

4. The vehicle air filtration system of claim 2, wherein the second seating row includes first, second, and third seating assemblies, and wherein the second inlet assembly includes a first inlet that extends in a first direction proximate each of the first, second, and third seating assemblies, and wherein the second inlet assembly includes a second inlet that extends in a second direction between the first and second seating assemblies and a third inlet that extends in the second direction between the second and third seating assemblies.

5. The vehicle air filtration system of claim 2, wherein the at least one fan includes a first fan fluidly coupled to the first inlet assembly and a second fan fluidly coupled to the second inlet assembly.

6. The vehicle air filtration system of claim 1, wherein the air filter assembly includes a housing coupled to the headliner, wherein the at least one fan, the light source, and the first air filter are disposed within the housing.

7. The vehicle air filtration system of claim 1, further comprising:
a controller communicatively coupled to the at least one fan, wherein the controller is communicatively coupled to at least one of a restraint control module, a body control module, and a climate control module.

8. The vehicle air filtration system of claim 7, wherein the controller activates the at least one fan to draw air from the interior compartment to the air filter assembly in response to a signal from at least one of the restraint control module, the body control module, and the climate control module.

9. An air filtration system for a vehicle, comprising:
a first inlet assembly;
a second inlet assembly in fluid communication with the first inlet assembly;
a housing;
a first fan disposed within the housing and in fluid communication with the first inlet assembly;
a second fan disposed within the housing in fluid communication with the second inlet assembly;
a light source disposed within the housing proximate the first and second fans, wherein the light source emits ultraviolet light;
a filter disposed within the housing proximate the first and second fans; and
an outlet in fluid communication with the first and second inlet assemblies, wherein air is drawn into the housing by the first and second fans, subjected to the ultraviolet light, and expelled via the outlet.

10. The air filtration system of claim 9, further comprising:
a controller communicatively coupled to the first and second fans, wherein the controller activates the first and second fans in response to a signal from at least one of a restraint control module, a body control module, and a climate control module.

11. The air filtration system of claim 10, wherein the controller activates the first fan in response to a first seatbelt switch signal detected by the restraint control module and the second fan is activated in response to a second seatbelt switch signal detected by the restraint control module.

12. The air filtration system of claim 9, wherein the filter is a high efficiency particulate air filter.

13. The air filtration system of claim 9, wherein the first inlet assembly includes a first inlet extending in a first direction and a second inlet extending in a second direction, wherein the second inlet assembly includes a first inlet extending in the first direction and a second inlet extending in the second direction, wherein the first direction is different than the second direction.

14. The air filtration system of claim 9, wherein the outlet is defined in a headliner.

15. The air filtration system of claim 9, wherein the outlet is in fluid communication with a heating, ventilation, and air conditioning system.

16. A method of filtering air in a vehicle, comprising:
detecting an activation signal;
activating at least one fan in response to the activation signal;
drawing air through a headliner inlet assembly into a housing via a vacuum effect produced by the at least one fan;
emitting an ultraviolet light within the housing;
directing the air through an air filter; and
expelling the air into an interior compartment.

17. The method of claim 16, wherein the step of detecting the activation signal includes detecting at least one of a passenger on a seating assembly, a vehicle ignition activation, and an activation of a heating, ventilation, and air conditioning system as the activation signal.

18. The method of claim 16, wherein the step of drawing air through the headliner inlet assembly includes drawing the air from proximate a first seating row in the interior compartment through a first inlet of the headliner inlet assembly via a first fan of the at least one fan and drawing the air from proximate a second seating row in the interior compartment through a second inlet of the headliner inlet assembly via a second fan of the at least one fan.

19. The method of claim 16, further comprising:
directing the air through a heating, ventilation, and air conditioning system.

20. The method of claim 16, wherein the step of emitting the ultraviolet light within the housing includes subjecting the air to the ultraviolet light as the air travels through the housing before traveling through the air filter.

* * * * *